United States Patent [19]

Gordon et al.

[11] 3,960,020

[45] June 1, 1976

[54] LIQUID ASPIRATING PROBE ASSEMBLY OF A SUPPLY ANALYZER

[75] Inventors: Abraham Gordon, Teaneck, N.J.; Stanford L. Adler, Monsey, N.Y.

[73] Assignee: Technicon Instruments Corporation, Tarrytown, N.Y.

[22] Filed: Dec. 30, 1974

[21] Appl. No.: 537,615

[52] U.S. Cl............................................ 73/423 A
[51] Int. Cl.².......................................... G01N 1/14
[58] Field of Search..................... 73/423 A; 23/259

[56] References Cited
UNITED STATES PATENTS

| | | | |
|---|---|---|---|
| 3,748,911 | 7/1973 | Rousselet | 73/423 A |
| 3,764,041 | 10/1973 | Noll | 23/259 |

*Primary Examiner*—S. Clement Swisher
*Attorney, Agent, or Firm*—S. P. Tedesco; Stephen E. Rockwell

[57] ABSTRACT

An aspirating probe which has a travel from a lower position in which it is immersed in a liquid in a receptacle to an upper position in which it clears the receptacle, carrying with it in its movement to the upper position a washing device to wash the interior and exterior thereof when in the last-mentioned position.

14 Claims, 7 Drawing Figures

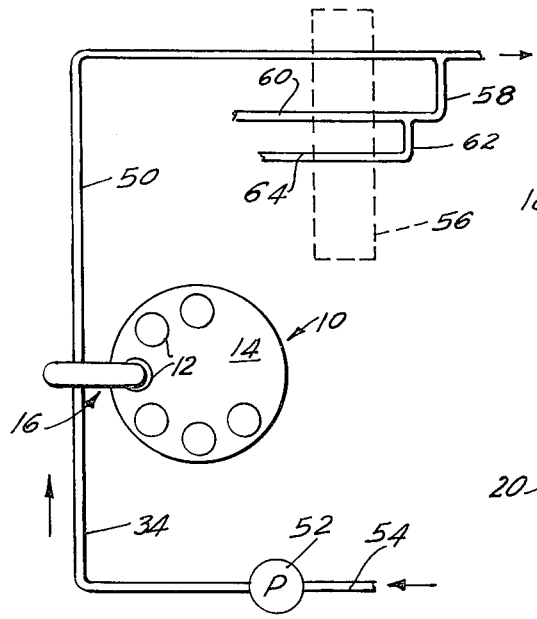
FIG. 1
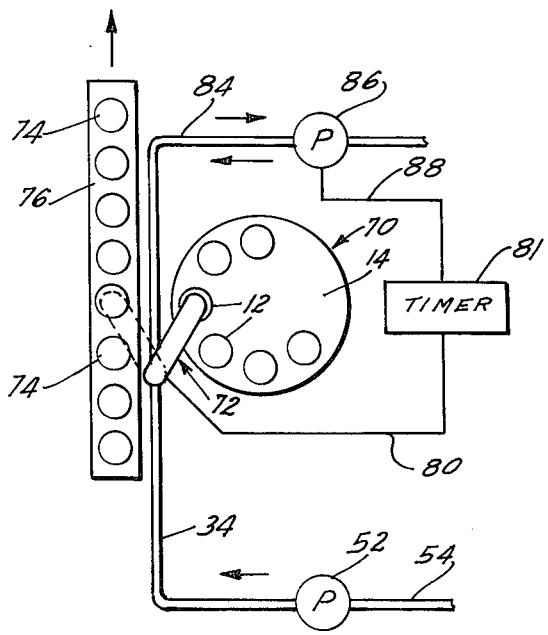
FIG. 4
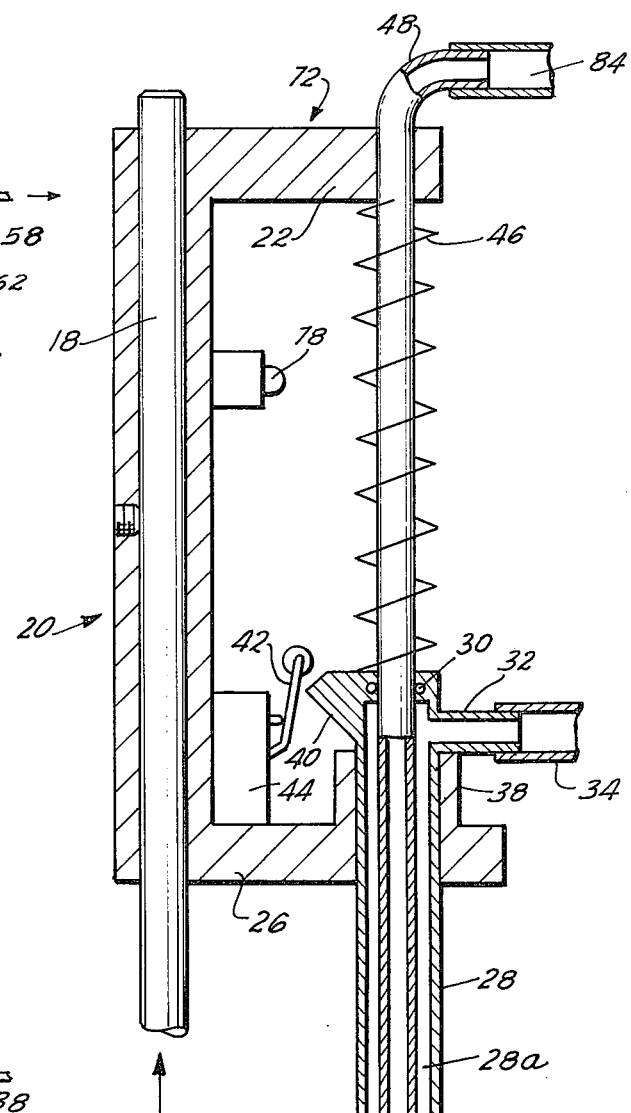
FIG. 5
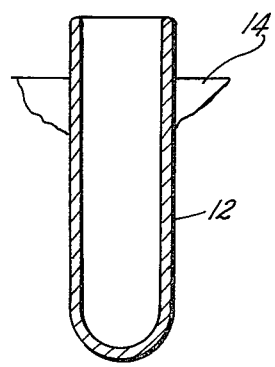

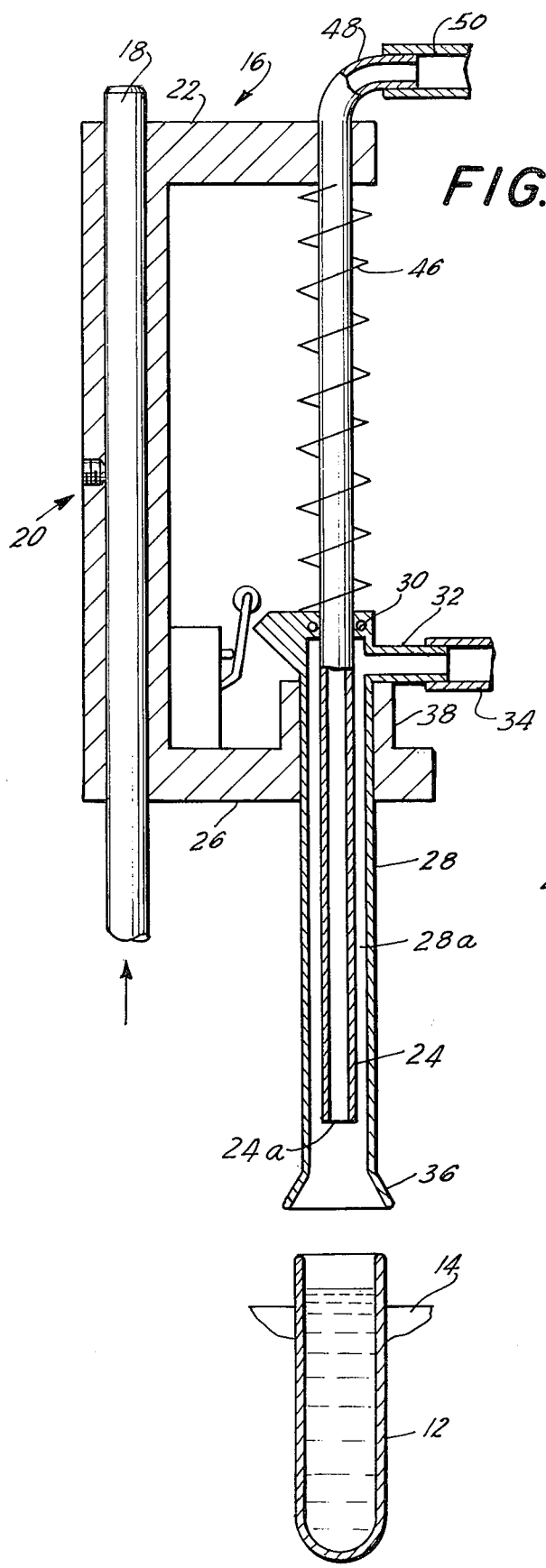
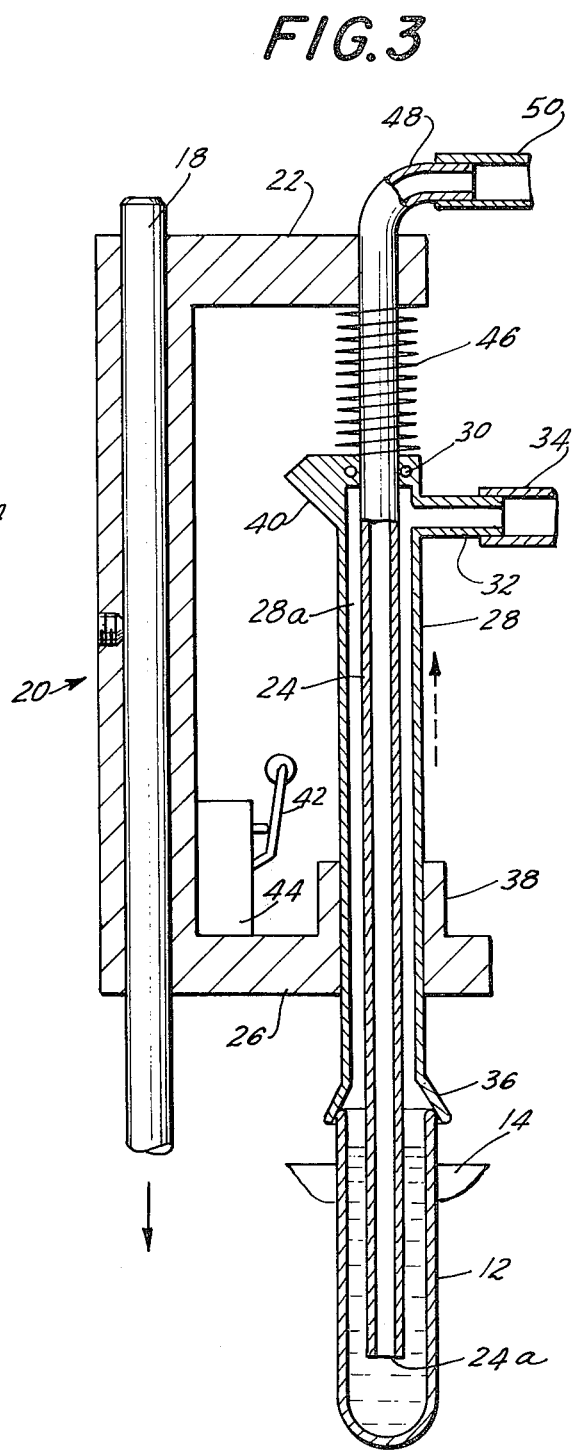
FIG. 2
FIG. 3

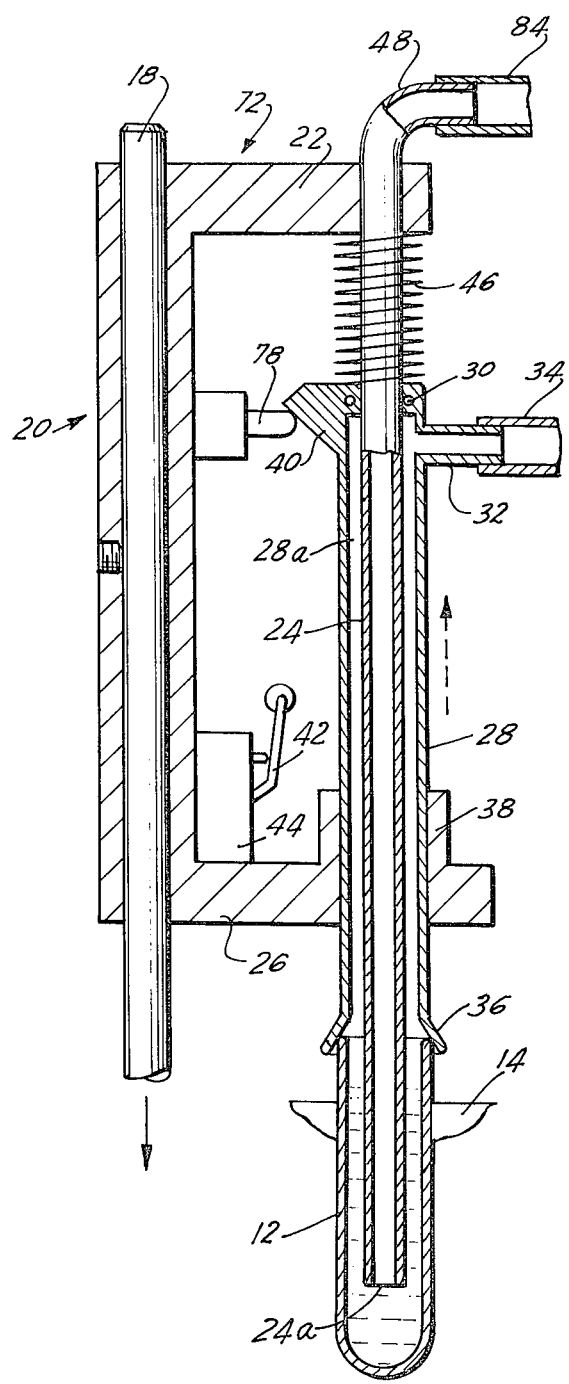
FIG.6
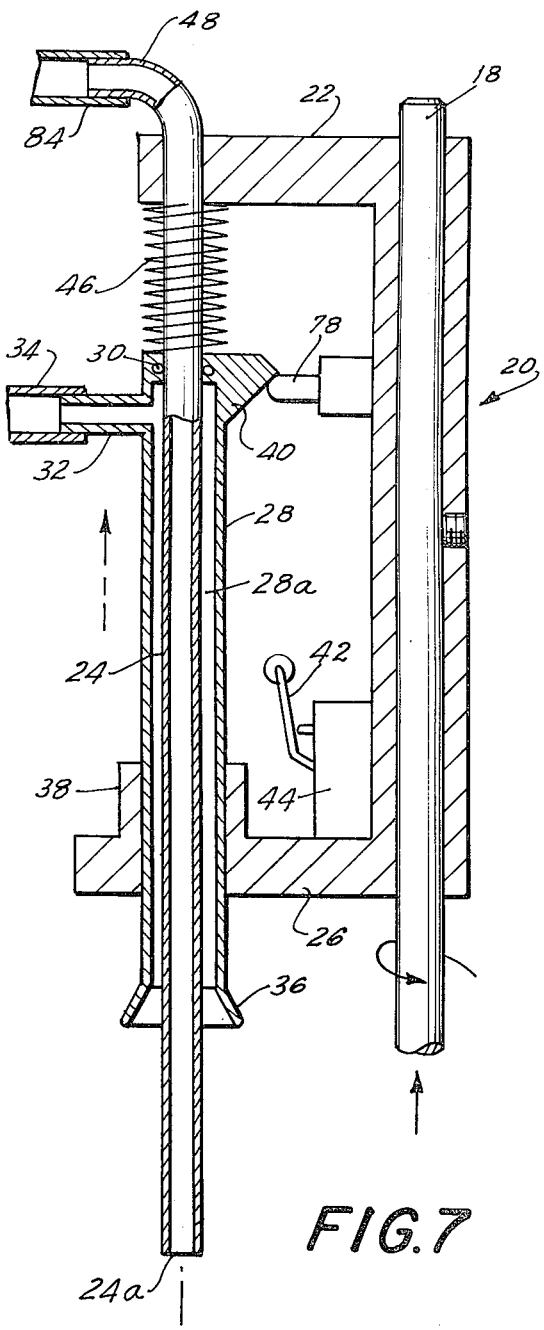
FIG.7
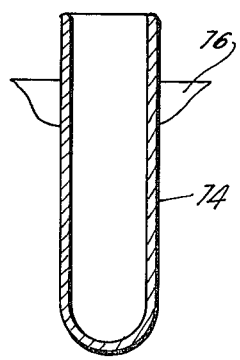

LIQUID ASPIRATING PROBE ASSEMBLY OF A SUPPLY ANALYZER

BACKGROUND OF THE INVENTION

1. Field of the Invention

This invention relates to an aspirating probe assembly useful in automated sample analysis and having a device associated therewith for washing the interior and exterior of the probe when the probe is not immersed in a liquid for aspitation thereof.

2. Prior Art

Heretofore, an aspirating probe has been associated with a sampler for the supply of a series of liquid samples for analysis seriatum. The samples may be a series of discrete blood serum specimens, each of which is supported and confined in a cup of a series of cups supported on a motor-driven turntable of the sample. The probe has been provided with a support for movement of the probe into the cup then indexed therewith for aspiration of the sample and then into the liquid within a stationary wash receptacle associated with the sampler for aspiration of wash liquid before the probe enters the next sample cup after movement of the turntable. Between immersions in sample and wash liquids, the probe has aspirated an immiscible fluid such as air and the resultant stream flowing from the probe has been segmented by segments of air and wash liquid, which segmentation of the sample stream preserves the integrity of the different samples. The segmentation is such that a wash liquid segment is located intermediate each sample and its neighbor and an air segment is located between each wash liquid segment and the adjoining sample as described in de Jong U.S. Pat. No. 3,134,263.

The probe assembly and sampler of Negersmith et al U.S. Pat. No. 3,266,322 accomplishes the same result described above but in a different way. In the latter, the stationary wash receptacle is disposed above the sample cup indexed with a probe which unlike the probe utilized in the de Jong disclosure has no angular movement on a verticle axis but has a similar up and down motion. The wash receptacle has vertically aligned openings above the sample cup indexed therewith, and the surface tension of the liquid within the receptacle is sufficient to prevent the wash solution from escaping through the small lower opening in the receptacle into the sample cup. As the probe leaves the sample cup, air is aspirated therein until the probe rises within the wash receptacle at which time the exterior of the probe is washed by the surrounding liquid and wash liquid is aspirated into the probe. Subsequently, the probe leaves the liquid in the wash receptacle in its upward movement and again aspirates air.

In Bannister et al U.S. Pat. No. 3,719,086, a stationary wash receptacle is provided over the indexed sample receptacle, such as is provided in Negersmith et al. The lower end of the aspirating probe is plugged and the probe has lateral inlet openings therein above the plug for the liquid which it aspirates such as a sample, and more specifically, the serum or plasma of a blood sample within a centrifuged sample cup. As in the Negersmith et al construction, the probe aspirates air in this case through the lateral inlets therein, on upward movement of the probe on leaving the sample receptacle to an intermediate postion of the probe. On further upward movement of the probe, the lower end of the probe is retracted to a position in which the plugged lower end lies below a flushing chamber in a bore formed in the receptacle and fluid is flushed through the chamber around an upper part of the probe and is aspirated from the chamber into the interior of the probe through the aforementioned inlet openings which are then disposed within the chamber. The plugged end of the probe within the aforementioned bore lies between the aforementioned chamber and a lower scavenging chamber from which fluid, mostly air, is sucked by a vacuum. It is pointed out by the patentees that there may be some flow of fluid from the chamber through the bore around the plugged section of the probe to the scavenging chamber. However, it appears that the bottom of the probe is not fully washed on the exterior thereof, and this may lead to contamination by the probe movements of one sample by another.

The aforementioned patents are believed to be typical of the prior art. It is proposed to overcome the difficulties with this prior art.

SUMMARY OF THE INVENTION

It is an object of the invention to provide a probe for aspirating liquid used in automated analysis, which has improved wash. Another object is to provide an aspirating probe which has a travel from a lower position in which it is immersed in the liquid in a receptacle for aspiration thereof to an upper position in which it clears the receptacle, carrying with it in movements intermediate these positions a washing device to wash the interior and exterior thereof when in the upper position. Further objects of the invention will appear from the following detailed description of the preferred embodiments of the invention.

BRIEF DESCRIPTION OF THE DRAWINGS

In the drawings:

FIG. 1 is a schematic diagram in fragmentary form of a portion of a liquid sample analyzer including a sampler and a probe assembly, embodying the invention;

FIG. 2 is a fragmentary side elevational view, partially in section, illustrating the probe assembly in the upper position thereof;

FIG. 3 is a view similar to FIG. 2 and illustrating the probe immersed in a liquid sample in a receptacle, for aspirating such liquid;

FIG. 4 is a diagramatic view similar to FIG. 1 showing a modified form of the invention wherein the probe assembly is utilized for both aspirating and dispensing liquid;

FIG. 5 is a view similar to FIG. 2 illustrating the probe of FIG. 4 in raised position:

FIG. 6 is a view similar to FIG. 3 illustrating the probe of FIG. 4 in lower position to aspirate liquid from a container thereof; and FIG. 7 is a view illustrating the probe of FIG. 4 in dispensing condition.

DETAILED DESCRIPTION OF THE PREFERRED EMBODIMENT

In FIG. 1 there is shown a sampler indicated generally at 10, to supply in this form a series of liquid samples sequentially for continuous-flow-type analysis. In the illustrated form, the samples may be a series of discrete blood serum samples, each of which samples is supported and confined in a cup 12 of a series of cups supported on a motor-driven turntable 14 of the sampler. Associated with the sampler, is a probe assembly, indicated generally at 16, provided on a vertical support including a shaft 18 (FIG. 2) for vertical movement of the probe assembly. The turntable 14 of the sampler may be driven in the manner described in de Jong U.S. Pat. No. 3,134,263, and the support shaft of the probe assembly 16 may be moved rectilinearly in an up and down direction by the structure of that patent. However, inasmuch as the support shaft 18 has no angular movement the cam 80 and cam follower 90 of that patent are omitted. The turntable 14 is rotated periodically to successively present each sample cup 12 to the probe assembly 16.

As shown in FIG. 2, the probe assembly 16 includes a member 20 of C shape having upper and lower horizontally extending arms provided with coaxial holes therethrough. A probe tube 24 is fixed in the hole of the upper arm 22 and extends downwardly a distance through the hole in the lower arm 26 of the member 20, the tube being part of the probe assembly 16. A tubular sheath element 28 of the probe assembly is vertically slideable on the probe tube 24 within limits. The upper end of the element 28 also is closed in fluid-tight relation around the probe tube 24, the structure including a sliding seal and bearing assembly 30. The probe 24 and the sheath 28 define an annular chamber 28 a therebetween.

Adjacent the upper end thereof the sheath or tubular element 28 has a tubular lateral inlet 32 connected to the outlet of a compressible pump tube 34. The lower end of the sheath element 28 is outwardly tapered, as at 36, so as to engage over and against the mouth of a cup 12 as will appear more fully hereinafter. Downward movement of the sheath element 28 around the probe 24 is limited by a collar 38 fixed to the arm 26, which extends around the sheath and in the condition shown in FIG. 2 provides an abutment for the lateral tubular inlet 32. At the upper end thereof, the sheath 28 has a lateral extension 40 of the angular configuration shown which cooperates with the actuator 42 of a switch 44. A compression spring 46 embraces the probe tube 24 and has one end bearing on the upper arm 22 of the support 20 and the other end thereof bearing against the top of the sheath element 28. The compression spring 46 urges the sheath element downwardly, and it is to be noted that in its fully extended position of FIG. 2 the bottom of the sheath 28 extends a distance below the lower extremity of the tube 24. The upper end of the probe 24 has an outlet 48 connected to the inlet of a compressible pump tube 50.

Turning once again to FIG. 1, it can be seen that a pump 52 is interposed in the tube 34, the latter having an inlet end 54 connected to a non-illustrated source of wash solution which may be water. The pump tube 50 extends through a pump 56 which may be of the peristaltic type. A compressible pump tube 58 extends through the pump 56 and has an inlet end 60 connected to a non-illustrated source of a reagent which may be Liebermann-Burchard reagent for determination of cholesterol in each of the successive blood serum samples analyzed in a non-illustrated manner. The outlet end of the tube 58 is connected to the tube 50 downstream from the pump 56. A pump tube 62 extends through the pump 56 and has an inlet end 64 open to the atmosphere for conveying air through the pump tube 62. The outlet end of the pump tube 62 is connected to the compressible pump tube 58 downstream of the pump to segment with air the reagent flowing in pump tube 58 prior to the latter's introduction into the flowing stream in pump tube 50 which directs the treated stream therein to analysis.

It is to be noted that in the condition of probe assembly 16 illustrated in FIG. 2, the probe assembly is in its raised position on the shaft 18 and in a position to be lowered toward the indexed sample cup associated therewith. In this condition the pump 54 is operative to pump wash solution through the inlet 32 in the sheath 28 to fill the annular chamber 28 a defined between the tube 24 and the sheath 28, with the flow in such chamber being in a downward direction around the tube 24. When such flow of wash solution reaches the lower end of the tube 24 within the sheath, the suction at the inlet end of the tube 24 is sufficient to draw the entire volume of such flow in the chamber 28a, together with some air drawn through the open lower end of the sheath 28, into the tube 24 and upwardly therein through the outlet 48 of the tube 24 into the tube 50 under the influence of the pump 56. This washes the exterior of the tube 24 to prevent contamination. The stream of wash liquid flowing in the probe tube 24 and the tube 50 cleanses the interior of such tubing such as the tubing 24, 50 and the non-illustrated tubing downstream thereof in the analyzer.

As the probe assembly 16 moves downwardly with the shaft 18 from the position of FIG. 2, the lower end of the outwardly tapered sheath engages the cup 12 therebeneath forcing the sheath 28 upwardly against the force of the spring 46, and in so doing the projection 40 of the sheath trips the actuator 42 of the switch 44 which stops the pump 54 and hence the flow of wash liquid through the probe assembly. Any remaining wash solution in the sheath is aspirated by the tube 24. Subsequently, as tube 24 continues downwardly relative to the sheath 28 air is aspirated into the tube 24 to later form an air segment therein. Preferably, no airtight connection exists between the sheath 28 and the cup 12. As the relative movement of the tube 24 and the sheath 28 is continued in this direction, the tube 24 enters the liquid in the cup 12 and commences to aspirate the sample liquid. When sufficient sample has been aspirated in this manner, the shaft 18 rises carrying with it the probe support in the form of the member 20 of C shape which carries the tube 24 upwardly relatively to the sheath 28. As the lower inlet end of the tube 24, indicated at 24a, clears any remaining liquid in the sample cup 12 moving relatively to the sheath 28 and prior to any movement of the latter in an upward direction, the tube 24 aspirates air which later forms an air segment in the stream in the probe assembly and in the pump tube 50. As the upward movement of the tube 24 travels to return to the position of FIG. 2 the projection 40 of the sheath trips the actuator 42 of the switch 44 thereby commencing operation of the pump 52 to once again introduce wash solution to the inlet 32 to first wash away the vestiges of the last sample on the exterior of the probe tube 24, and then flow upwardly in the probe 24 to cleanse the interior of the latter. As the support member 20 rises with the shaft 18, the spring 46 retains the sheath 28 engaged with the cup 12 until the collar 38 of the member 20 engages the tubular fluid inlet 32 and thereafter lifts the sheath 28 bodily with the tube 24 so that the former clears the cup 12. The pump 52 continues to operate and the wash solution continues to be supplied, while the turntable 14 of the sample has been rotated to index the next sample cup 12 with respect to the probe, until the probe assembly 16 has descended sufficiently for the cycle to be repeated as the sheath 36 engages the last-mentioned cup 12 and is displaced upwardly thereby, once again actuating the switch and thereby terminating operation of the pump 52 and permitting air to be aspirated upwardly in the tube 24 prior to entry of the latter into the liquid in the last-mentioned cup 12.

In the aspirator-dispenser modification of the invention shown in FIGS. 4–7, like numerals identify like parts. The sampler indicated generally at 70 (FIG. 4) is in all respects other than the probe assembly similar to the sampler 10 for delivery successively of a series of, say, blood serum samples, except that unlike the sampler 10 the shaft 18 (FIG. 5) supporting the probe assembly, indicated generally at 72, has an angular movement as well as an up and down movement as described in the aforementioned de Jong U.S. Pat. No. 3,134,263. The construction and arrangement is such that when the probe assembly supported by the shaft 18 is in the upper condition of FIG. 5 after aspirating a sample it may thereafter swing on the axis of the shaft 18 to a position to dispense the sample or a portion thereof to an indexed one of a series of sample-receiving receptacles 74 supported in a movable tray 76 for indexing movement in a conventional manner in the direction of an arrow FIG. 4.

The probe assembly 72 is like the previously described probe assembly in all respects except that it has an added element in the form of a solenoid-operated latch 78 supported on the vertical leg of the support member 20 a distance above the switch 44. The solenoid operated latch 78 may be energized to a latched position thereof and may be alternately energized for retraction of the latch. The operation of the probe assembly is identical to that of the probe assembly 16 previously described except that as the probe assembly descends on a sample cup 12 and the sheath 28 is deflected upwardly by the last-mentioned cup for aspiration of the sample as shown in FIG. 6, the latch 78 is operated to latch the sheath in its relatively retracted position of FIG. 6 by engagement of the latch with the lateral projection 40 on the sheath 28.

Turning again to FIG. 4, a timer may be provided as shown which has an output to the input of a cable 80 which has an output to the solenoid-operated latch 78 to effect extension and retraction of the latch 78. The timer also has an output to an input of a cable 82 which has an output to the sampler controlling the indexing of the turntable 14 to successively index sample cups 12 with the probe assembly 72 and also to control the movements of the probe assembly 72. As shown in FIG. 5, the outlet 48 of the tube 24 is coupled to the inlet of a tube 84 and a reversible pump 86 is interposed in the tube 84. The tube 84 has an outlet to waste. The timer has an output to an input of a cable 88 having an output to the pump 86 to activate the latter periodically in one direction or the other.

When the probe assembly 72 is in the condition of FIG. 5 and about to move downwardly with the shaft 18 toward the sample delivery cup 12 spaced therebelow the probe assembly is in the aforementioned wash mode and the pump 52 is energized to supply wash solution to the probe inlet 32 through the pump tube 34. The wash solution flowing around the lower portion of the tube 24 is sucked upwardly through the lower inlet 24a of the tube 24 to wash the interior of the tube 24 as well, and is directed by the tube 24 into the tube 84 which delivers the wash liquid to waste through the oulet of the last-mentioned tube. The last-mentioned position of the probe assembly 72 is a rest position.

When the probe assembly 72 moves from the position of FIG. 5 to the position of FIG. 6 in which the tube 24, after first aspirating air following the wash liquid, aspirates the liquid in the sample-receiving cup 12, which movement deflects the sheath upwardly, the timer actuates latch 78 to extend it to the latched position of FIG. 6. At this time, the aspirated sample has filled the tube 84 a distance short of the pump 86. When the probe assembly 72 returns to the upper position so that the assembly clears the receptacle 12, the sheath remains latched and continues in this latched condition while the shaft 18 swings the probe assembly to the position of FIG. 7. It is to be understood that prior to this bodily upward movement and subsequent swinging movement of the probe assembly 72, the pump 52 is deenergized by actuation of the switch 44 and the pump 86 is deenergized by the timer. After the probe assembly 72 has reached the angular position of FIG. 7 above the indexed sample-receiving cup 74 in the tray 76, the timer energizes the pump 86 in the reverse direction to dispense all or a portion of the sample in the tubes 84, 24 through the probe assembly into the sample-receiving cup 74 spaced below the probe assembly. Thereafter, the probe assembly 72 under the control of the timer begins its return travel toward the position of FIG. 5 and during this return the timer retracts the latch 78 so that the tube 24 and the sheath 28 assume the relative positions one to the other shown in FIG. 5 which once again places the probe assembly in the wash mode. It is to be understood that as the probe assembly is placed in the wash mode, the pump 86 is reversed by the timer to aspirate fluid through the tube 24. During this period the turntable 14 and the tray 76 are moved to move up into indexed position the next following sample-delivery cup 12 and sample-receiving cup 74. The wash solution is directed to waste through the tube 84 as the next cycle starts, washing away the vestiges in the tube 84 of the last sample. While in the illustrated forms there has been shown and described means to relatively index the probe assembly with successive liquid receptacles, it is to be understood the invention does not require this means such as the sampler, as the liquid receptacles may be presented to the probe assembly of the invention manually. In such an embodiment, the user lifts the liquid receptacle under the probe assembly so as to engage the mouth of the receptacle with the open lower end of the probe sheath 28 and deflect the sheath upwardly so that the probe extends into the liquid within the receptacle for aspiration of such liquid. Further, in such an embodiment the probe 24 need not have any vertical movement. In addition, it will be apparent that the invention also contemplates an arrangement wherein a liquid receptacle is raised mechanically to deflect the probe sheath 28 upwardly and achieve on such movement immersion of the probe into the liquid in the receptacle.

While plural forms of the liquid aspirating probe assembly of a sample analyzer have been illustrated and described, it will be apparent, especially to those versed in the art, that invention may take other forms and is susceptible of various changes of details without departing from the principles of the invention.

What is claimed is:

1. A sample analyzer comprising an aspirating probe element having an inlet for immersion successively in liquids contained in a series of receptacles and for relative retraction to an upper position prior to immersion in the liquid of another receptacle, and means flushing a wash solution down the exterior of said probe element in said upper position and drawing off substantially all the flushed solution through said probe inlet.

2. Apparatus as defined in claim 1, wherein: said means flushing said probe element and drawing off said flushed solution comprises a sheath element spaced outwardly around said probe element and through which sheath element said wash solution is introduced.

3. Apparatus as defined in claim 2, wherein: said sheath element has an opening in the bottom thereof.

4. Apparatus as defined in claim 2, further including a support element for said probe element and movable therewith, said sheath element being supported from said support member.

5. Apparatus as defined in claim 3, wherein: said probe inlet is disposed a distance upwardly from said sheath opening when the probe element is in said upper position thereof, one of said elements being mounted for sliding movement relatively to the other, said slidable element having means by which it is moved relatively to the other to extend said probe element from the sheath element for immersion in a liquid in one of said receptacles.

6. Apparatus as defined in claim 5, wherein: said slidable element is said sheath element, and said means by which said sheath element is moved comprises a portion of said sheath element which on relative downward movement of said probe element is engageable by the mouth of one of said receptacles to deflect the sheath upwardly.

7. Apparatus as defined in claim 6, wherein: said sheath element is spring biased in a downward direction.

8. Apparatus as defined in claim 6, further including means to relatively index said probe with said series of liquid receptacles successively.

9. Apparatus as defined in claim 8, wherein: said sheath portion comprises a tapered part of the sheath which engages over and against the mouth of said receptacle.

10. A sample analyzer, comprising: a dipping probe for immersion successively in liquids contained in a series of receptacles and for relative movement to a raised position clear of the receptacle prior to immersion in the liquid of another receptacle, means bodily movable at least in part with said probe in an upward direction to said raised non immersed position thereof to flush a wash solution down the exterior of said probe and draw off such wash solution in the last-mentioned probe position.

11. Apparatus as defined in claim 10, wherein: said probe is an aspirating probe having at least an upper hollow portion thereof with an inlet thereinto, and said means to flush said probe with wash solution and draw off such flushed solution includes means drawing off such flushed solution through the interior of said probe to cleanse it.

12. Apparatus as defined in claim 11, wherein: said probe is an aspirating-dispensing probe, further including means supporting said probe and moving it in said raised position thereof laterally to a dispensing position with respect to a liquid-receiving receptacle, and said means to flush said probe with wash solution and draw off such flushed solution is operative subsequent to the dispensing of the liquid from said probe.

13. Apparatus as defined in claim 12, wherein: said means to flush said probe with wash solution and draw off such flushed solution includes a sheath outwardly and around said probe and forming with the latter a chamber into which said wash solution is introduced, said sheath being slideably supported by said means supporting said probe, for extension of said probe from the sheath on aspiration of liquid from one of said receptacles and on dispensing of liquid from said probe.

14. Apparatus as defined in claim 13, further including means supporting said sheath in retracted position while said probe is removed from one of said series of receptacles and thereafter dispenses liquid.

* * * * *